United States Patent
Li et al.

(10) Patent No.: US 12,163,276 B2
(45) Date of Patent: Dec. 10, 2024

(54) COMPOSITION AND METHOD FOR ODOR REDUCTION AND BACTERIAL CONTROL ON A TEXTILE

(71) Applicant: MICROBAN PRODUCTS COMPANY, Huntersville, NC (US)

(72) Inventors: Yihong Li, Huntersville, NC (US); Ivan Wei Kang Ong, Charlotte, NC (US); Xiuzhu Fei, Charlotte, NC (US)

(73) Assignee: MICROBAN PRODUCTS COMPANY, Huntersville, NC (US)

( * ) Notice: Subject to any disclaimer, the term of this patent is extended or adjusted under 35 U.S.C. 154(b) by 0 days.

(21) Appl. No.: 17/845,924

(22) Filed: Jun. 21, 2022

(65) Prior Publication Data

US 2022/0411994 A1    Dec. 29, 2022

Related U.S. Application Data

(60) Provisional application No. 63/216,321, filed on Jun. 29, 2021.

(51) Int. Cl.
| | | |
|---|---|---|
| D06M 13/203 | (2006.01) | |
| D06B 3/10 | (2006.01) | |
| D06B 3/18 | (2006.01) | |
| D06M 16/00 | (2006.01) | |

(52) U.S. Cl.
CPC ........... *D06M 13/2035* (2013.01); *D06B 3/10* (2013.01); *D06B 3/18* (2013.01); *D06M 16/00* (2013.01)

(58) Field of Classification Search
CPC ...... D06M 13/2035; D06B 3/10; D06B 3/18; D06M 16/00
See application file for complete search history.

(56) References Cited

U.S. PATENT DOCUMENTS

| | | | |
|---|---|---|---|
| 2014/0275264 A1* | 9/2014 | Consalo | C12N 1/20 514/570 |
| 2018/0110700 A1 | 4/2018 | Dihora et al. | |
| 2019/0024027 A1 | 1/2019 | Dowdle | |
| 2019/0352843 A1 | 11/2019 | Szarvas et al. | |

FOREIGN PATENT DOCUMENTS

| | | | | |
|---|---|---|---|---|
| CN | 102796472 A | * | 11/2012 | |
| CN | 104073153 A | * | 10/2014 | |
| CN | 104087051 A | * | 10/2014 | |
| CN | 104288181 A | * | 1/2015 | |
| CN | 104562681 A | * | 4/2015 | |
| CN | 105862406 A | * | 8/2016 | |
| CN | 106675225 A | * | 5/2017 | |
| CN | 107556924 A | * | 1/2018 | |
| DE | 102009002687 A1 | * | 11/2010 | ............. A61L 2/232 |
| WO | 2020/018891 A1 | | 1/2020 | |
| WO | 2021/076526 A1 | | 4/2021 | |

OTHER PUBLICATIONS

International Search Report and Written Opinion for PCT Application No. PCT/US2022/34602, dated Sep. 9, 2022, all enclosed pages cited.

* cited by examiner

*Primary Examiner* — Anthony J Green
(74) *Attorney, Agent, or Firm* — Shumaker, Loop & Kendrick, LLP

(57) ABSTRACT

A composition and method for durable odor control on a textile are provided. The composition contains benzoic acid; a salt of benzoic acid; non-benzoic acid, a salt of non-benzoic acid, or a combination thereof. The composition may further contain an optional binder. Methods of application of the composition include padding and exhaustion.

8 Claims, No Drawings

COMPOSITION AND METHOD FOR ODOR REDUCTION AND BACTERIAL CONTROL ON A TEXTILE

CROSS-REFERENCE TO RELATED APPLICATION

This application claims priority from U.S. Provisional Patent Application No. 63/216,321 filed on Jun. 29, 2021, in the United States Patent and Trademark Office. The disclosure of which is incorporated herein by reference in its entirety.

FIELD OF THE INVENTION

The present invention relates to a composition and method for odor control, more particularly to a composition and method for durable odor control on a textile.

BACKGROUND OF THE INVENTION

Current bacterial control on textile garments relies heavily on the use of metal containing actives, such as zinc. These "heavy metal" presences in process effluent water in textiles mills has been an issue of concern for environmental policy and regulators. It will ultimately result in an inability to utilize zinc pyrithione to reduce odor and stain causing bacteria on textile surfaces.

Alternatively, the use of organic molecules, such as quaternary ammonium silanes, phenolics, and azoles, can be leveraged to treat textile surfaces. These chemistries require extensive formulary efforts to reduce hydrophobicity, increase durability.

This invention provides an antimicrobial solution for textile substrates which meets a new regulatory requirement, does not impart hydrophobicity, and provides good durability.

SUMMARY OF THE INVENTION

The present invention relates to a composition and method for durable odor control on a textile.

In an embodiment of the invention, a composition is provided. The composition comprises: benzoic acid, a salt of benzoic acid, non-benzoic acid, or a combination of the non-benzoic acid and the salt of non-benzoic acid; and an optional binder.

In an embodiment of the invention, a composition is provided. The composition comprises: sodium benzoate, and citric acid.

In an embodiment of the invention, a composition is provided. The composition comprises: a component selected from the group consisting of benzoic acid, a salt of benzoic acid, and a combination thereof; and a binder.

In an embodiment of the invention, a method is provided. The method comprises mixing benzoic acid and/or a salt of the benzoic acid, and an optional binder. The method may further comprise exhausting a textile using the mixture in an exhaustion bath.

In an embodiment of the invention, a method is provided. The method comprises mixing sodium benzoate with a non-benzoic acid and/or a salt of the non-benzoic acid, and an optional binder. The method may further comprise exhausting a textile using the mixture in an exhaustion bath.

In an embodiment of the invention, a method is provided. The method comprises mixing benzoic acid and/or a salt of the benzoic acid, and an optional binder. The method may further comprise padding the mixture on a textile.

In an embodiment of the invention, a method is provided. The method comprises mixing sodium benzoate with a non-benzoic acid and/or a salt of the non-benzoic acid, and an optional binder. The method may further comprise padding the mixture on a textile.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

DESCRIPTION OF THE PREFERRED EMBODIMENTS

The following description of the embodiments of the present invention is merely exemplary in nature and is in no way intended to limit the invention, its application, or uses. The following description is provided herein solely by way of example for purposes of providing an enabling disclosure of the invention, but does not limit the scope or substance of the invention.

Further, the term "or" as used in this disclosure and the appended claims is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in," "at," and/or "on," unless the context clearly indicates otherwise. The phrase "in one embodiment," as used herein does not necessarily refer to the same embodiment, although it may.

The present invention provides a composition suitable to withstand the requirements of textile processing temperatures, water dispersibility, compatibility with acetic acid, and low skin toxicity profiles.

In an embodiment of the invention, the composition comprises a component selected from the group consisting of benzoic acid, a salt of benzoic acid, non-benzoic acid, a salt of non-benzoic acid, and a combination thereof. The composition may further comprise an optional binder.

A non-limiting example of a salt of benzoic acid is sodium benzoate.

Non-limiting examples of non-benzoic acid are sorbic acid, citric acid, lactic acid, acetic acid, L-glutamic acid, or a combination thereof.

Non-limiting examples of a salt of a non-benzoic acid are potassium sorbate, trisodium citrate, and a combination thereof.

Preferably, the binder comprises an acrylic.

In a preferred aspect of the invention, the composition comprises a combination of sodium benzoate and a non-benzoic acid. For example, sodium benzoate and a non-benzoic acid selected from the group consisting of sorbic acid, citric acid, lactic acid, acetic acid, L-glutamic acid, and a combination thereof.

It is surprisingly found that there is a synergistic effect achieved with a combination of sodium benzoate and a non-benzoic acid in regard to odor control and durability to home laundering when applied on a textile. Sodium benzoate and non-benzoic acid are in a weight ratio in a range of 1:3 to 10:1.

Preferably, the composition comprises sodium benzoate and citric acid. The composition of sodium benzoate and citric acid are preferably in a weight ratio in a range of 1:3 to 10:1. For example, experiments conducted below illustrate a ratio of sodium benzoate to citric acid in a 1:1 ratio. The composition may be in powder form, liquid form, or a combination thereof. Preferably, the composition is in powder form but also applicable in liquid form. The components of the composition can be added as a mixture or separately, either in powder form, liquid form, or a combination thereof.

In an aspect of the invention, methods of preparation and/or using are provided. Any number of textile application or treatment methods including, but not limited to, padding or exhaustion can be used.

A method of the invention comprises applying the composition of the invention to a textile by exhaustion. For example, the method comprises adding benzoic acid (and/or a salt of the benzoic acid), or sodium benzoate and a non-benzoic acid (and/or a salt of the non-benzoic acid), and an optional binder, to an exhaustion bath; exhausting a textile such as a fabric; and drying. Exhausting preferably occurs at a temperature in a range of 85° C. to 130° C. and/or for a period of time in a range of 20 minutes to 45 minutes.

A method of the invention comprises applying the composition to a textile by padding. For example, the method comprises adding benzoic acid (and/or a salt of the benzoic acid), or sodium benzoate and a non-benzoic acid (and/or a salt of the non-benzoic acid), and an optional binder to a padding bath; padding the composition on a textile such as a fabric; and curing at 130° C. to 160° C. for 45 seconds to 1 minute.

The binder is optional and may be added depending upon the final textile washing durability requirements. Preferably, the binder is an acrylic binder. However, it was surprisingly found that inclusion of the binder enhanced the already unexpected antimicrobial benefit.

Bacteria control on a textile material can be activated and enhanced by laundry process. Advantages of the present invention the composition of the present invention is non-hazardous and is applicable to most forms of textile manufacturing.

Example 1

Benzoic acid with an acrylic binder was padded on 100% polyester. Antimicrobial efficacy before and after 25 home laundry (HL) washes had been tested following AATCC TM100. Bacteria used for the test is kleb pneumoniae. Data is shown in Table 1. At both 0 HL and 25 HL significant log reduction were observed, and data was repeatable in different runs.

TABLE 1

| Log Reduction | Run1 (0HL) | Run2 (0HL) | Log Reduction | Run (25HL) | Run2 (25HL) |
|---|---|---|---|---|---|
| Raw Data | 4.7 | 4.7 | Raw Data | 4.4 | 3.4 |
| | 4.7 | 4.7 | | 1.6 | 3.4 |
| | 4.7 | 4.7 | | 3.9 | 1.7 |
| Avg. | 4.7 | 4.7 | Avg. | 3.3 | 2.8 |
| STDEV | 0 | 0 | STDEV | 1.2 | 0.8 |

Example 2

This example illustrates exhaustion results using a composition comprising sodium benzoate and a non-benzoic acid. The non-benzoic acid used was citric acid. The composition was applied on 100% polyester. The results were obtained from a mill trial. Test conditions were 16% applied based on weight of fabric (o.w.f.) and a 1:1 ratio of sodium benzoate to citric acid. Data are shown in Table 2.

TABLE 2

| | 0 HL | | 1 HL | | 5 HL | | 25 HL | | 50 HL | |
|---|---|---|---|---|---|---|---|---|---|---|
| | Kp | Sa | Kp | Sa | Kp | Sa | Kp | Sa | Kp | Sa |
| Run 1 | 0 | 0 | 0.2 | 1 | 1.2 | 2 | 1.8 | 2.2 | 1.8 | 2.9 |
| | 0 | 0 | 0 | 1.6 | 1.4 | 3.9 | 2.2 | 4.4 | 2 | 2.9 |
| | 0 | 0 | 0.1 | 1.8 | 1.7 | 3.4 | 2.7 | 2.7 | 1.8 | 3.2 |
| Run 1 Average | 0 | 0 | 0.1 | 1.5 | 1.4 | 3.1 | 2.2 | 3.1 | 1.9 | 3.0 |
| Run 2 | 0 | 0 | 0.8 | 0 | 1.4 | 3.4 | 1.9 | 3.9 | 1.8 | 4.7 |
| | 0 | 0 | 1.1 | 2.6 | 1.4 | 3.4 | 1.8 | 3.6 | 1.4 | 4.7 |
| | 0 | 0 | 0 | 1.9 | 1.2 | 3.5 | 2 | 4.2 | 1.8 | 4.2 |
| Run 2 Average | 0 | 0 | 0.6 | 1.5 | 1.3 | 3.4 | 1.9 | 3.9 | 1.7 | 4.5 |

Exhaustion efficacy had been tested following AATCC TM100 on 100% polyester. No efficacy had been detected before wash. Reduction rate of both kleb pneumoniae and *Staphylococcus aureus* were increased along with washing times.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

What is claimed is:
1. A treated textile comprising:
a textile material having an antimicrobial and anti-odor composition thereon,
wherein the antimicrobial and anti-odor composition consists of:
a salt of benzoic acid;
a non-benzoic acid selected from the group consisting of sorbic acid, citric acid, lactic acid, acetic acid, L-glutamic acid, trisodium citrate, potassium sorbate, and combinations thereof;

wherein the antimicrobial and anti-odor composition has a weight ratio of salt of benzoic acid to non-benzoic acid ranging from 1:3 to 10:1; and the antimicrobial and anti-odor composition reduces microbial growth on the textile after laundering.

2. The treated textile according to claim 1, wherein the salt of benzoic acid is sodium benzoate.

3. The treated textile according to claim 1, wherein the non-benzoic acid is a powder.

4. The treated textile according to claim 1, wherein the textile exhibits a 2.2 log reduction of *Klebsiella pneumoniae* after 25 home launderings and a 3.1 log reduction in *Staphylococcus aureus* after 25 home launderings.

5. The treated textile according to claim 1, wherein the textile exhibits a 1.9 log reduction of *Klebsiella pneumoniae* after 50 home launderings and a 3.0 log reduction in *Staphylococcus aureus* after 50 home launderings.

6. A treated textile comprising:
 a textile material having an antimicrobial and anti-odor composition thereon,
 wherein the antimicrobial and anti-odor composition consists of:
  sodium benzoate, and
  citric acid
  wherein the antimicrobial and anti-odor composition has a weight ratio of sodium benzoate to citric acid ranging from 1:3 to 10:1; and
 the antimicrobial and anti-odor composition reduces microbial growth on the textile after laundering.

7. The treated textile according to claim 6, wherein the textile exhibits a 2.2 log reduction of *Klebsiella pneumoniae* after 25 home launderings and a 3.1 log reduction in *Staphylococcus aureus* after 25 home launderings.

8. The treated textile according to claim 6, wherein the textile exhibits a 1.9 log reduction of *Klebsiella pneumoniae* after 50 home launderings and a 3.0 log reduction in *Staphylococcus aureus* after 50 home launderings.

* * * * *